United States Patent [19]
Matson et al.

[11] Patent Number: 5,338,738
[45] Date of Patent: Aug. 16, 1994

[54] CEREBRAL FUNCTION ENHANCERS: ACYCLIC AMIDE DERIVATIVES OF PYRIMIDINYLPIPERIDINES

[75] Inventors: Ronald J. Matson, Meriden; Joseph P. Yevich, Southington, both of Conn.

[73] Assignee: Bristol-Myers Squibb Company, New York, N.Y.

[21] Appl. No.: 49,749

[22] Filed: Apr. 19, 1993

[51] Int. Cl.$^5$ ................. C07D 401/04; A61K 31/505
[52] U.S. Cl. ..................................... 514/256; 544/322
[58] Field of Search ................ 514/256; 544/328, 329, 544/322

[56] References Cited

U.S. PATENT DOCUMENTS

| | | | |
|---|---|---|---|
| 3,717,634 | 2/1973 | Wu et al. | 260/256.4 |
| 4,423,049 | 12/1983 | Temple | 544/309 |
| 4,524,206 | 6/1985 | New et al. | 544/230 |
| 4,668,687 | 5/1987 | Yevich et al. | 514/252 |
| 4,826,843 | 5/1989 | Mattson et al. | 514/252 |
| 5,098,904 | 3/1992 | Mattson et al. | 514/256 |

OTHER PUBLICATIONS

Butler, et al., J. Med. Chem. 27, pp. 684–691 (1984).
Malawska, et al., "Synthesis and Pharmacological Properties of Some 2-Pyrrolidinone Mannich Bases", Polish Journal of Pharmacology, 34, pp. 373–382 (1982).

Primary Examiner—John M. Ford
Attorney, Agent, or Firm—Richard P. Ryan

[57] ABSTRACT

A series of acyclic amide derivatives of pyrimidinylpiperazines of Formula I

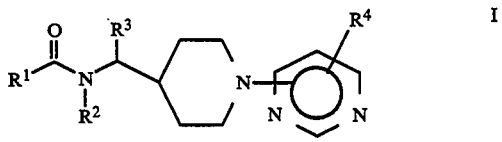

wherein $R^1$ is alkyl, phenalkyl, phenyl-hydroxyalkyl, phenyl and pyridinyl; $R^2$ and $R^3$ are hydrogen and alkyl; and $R^4$ is hydrogen, halogen, and trifluoromethyl.

Compounds of the invention can be incorporated into pharmaceutical compositions for use in enhancing cerebral function. The compounds are envisioned as being useful in restoration of cerebral function in degenerative disorders; in amnesia reversal; and in improvement of memory and learning processes.

10 Claims, No Drawings

CEREBRAL FUNCTION ENHANCERS: ACYCLIC AMIDE DERIVATIVES OF PYRIMIDINYLPIPERIDINES

BACKGROUND OF THE INVENTION

This invention generally pertains to heterocyclic carbon compounds having drug and bio-affecting properties and to their preparation and use. In particular, the invention is concerned with disubstituted piperidine derivatives wherein one substituent is an acyclic amide moiety linked by a bridging alkyl connector to one of the carbon ring positions of the piperidine ring and the other substituent is a pyrimidinyl ring system attached to the piperidine nitrogen atom. The compounds of this invention are cerebral function enhancers useful, for example, in treating various dementias due to degenerative processes as well as in enhancing memory and learning.

Clinical aspects of various degenerative dementias, as well as the socioeconomic problems they cause in affected populations, are well known to those skilled in the art. One will also appreciate that various drug treatments of these disorders are currently under study. Among such drugs are a class of drugs known as nootropic agents or, more commonly, cognition enhancers; some of which are currently undergoing clinical evaluation in patients diagnosed as having Alzheimer's disease, a serious and fairly common CNS disorder of the elderly. Many of these drugs under clinical study are members of a class of N-substituted 2-pyrrolidinone derivatives of structure

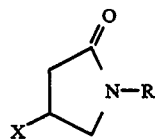

a: X=H; R=CH$_2$CONH$_2$(piracetam)
b: X=OH; R=CH$_2$CONH$_2$ (oxiracetam)
c: X=H; R=CH$_2$CONH[CH$_2$]$_2$N[CH(CH$_3$)$_2$]$_2$ (pramiracetam)

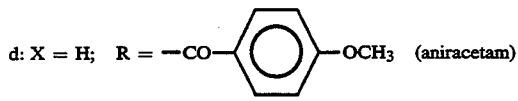

For a representative reference describing the testing and properties of a member of this series 1, see Butler, et al., J. Med. Chem., 27, pages 684–691 (1984). Preliminary clinical results with this class of agents, exemplified by structures 1a-d, indicate that these drugs may have some beneficial effects in treating senile dementias in the elderly.

Related art may be viewed in light of the following general structural formula (2).

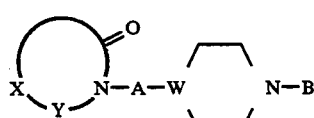

wherein X is usually C$_{2-4}$ substituted or unsubstituted alkylene; Y is carbonyl or methylene; A is a bridging moiety such as alkylene, alkanoyl, alkyleneamidoalkylene, and the like; W is nitrogen; and B is a pyrimidinyl, pyridinyl, or benzisothiazolyl ring system. Members of this series are reported to have psychotropic, anxiolytic, antiemetic, tranquilizing, cognitive enhancing, as well as other nootropic activities. For more detailed disclosure of these compounds, see: Yevich and Mattson, U.S. Pat. No. 4,668,687 issued May 26, 1987, Wu, et al., U.S. Pat. No. 3,717,634 issued Feb. 20, 1973; Temple, U.S. Pat. No. 4,423,049 issued Dec. 27, 1983; and New and Yevich, U.S. Pat. No. 4,524,206 issued Jun. 18, 1985.

Other subject matter related to formula 2 compounds was disclosed by Malawska, et al., in "Synthesis and Pharmacological Properties of Some 2-Pyrrolidinone Mannich Bases" in the Polish Journal of Pharmacology, 34, pages 373–382 (1982). They described a series of compounds, of which one subclass is represented by structural formula 3, which reportedly display analgesic properties as well as weak anti-inflammatory action.

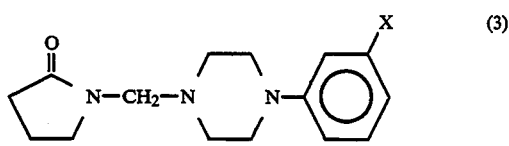

wherein X is hydrogen or chlorine.

The most relevant art is believed to be the patent to Mattson, et al., U.S. Pat. No. 4,826,843 issued May 2, 1989, wherein compounds of general formula 4 were disclosed as having cognition and memory enhancing activities.

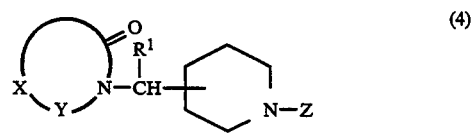

For Formula 4, X is an ethylene chain or 1,2-benzo ring; Y is carbonyl or methylene; R$^1$ is hydrogen or lower alkyl; and Z is an R$^2$, R$^3$-disubstituted diazinyl ring selected from pyridazine, pyrimidine, and pyrazine ring systems.

Mattson, et al., U.S. Pat. No. 5,098,904 issued Mar. 24, 1992 disclosed and claimed oxygenated derivatives of the formula (4) compounds.

The art compounds, as set forth supra, incorporate a lactam or lactim ring moiety at the compound's nondiazine terminus. The novel acyclic amide compounds described herein are structurally distinct cerebral function enhancing agents. There are no teachings in the art which would make these specific compounds of the instant invention anticipated or obvious.

SUMMARY OF THE INVENTION

The present invention is concerned with compounds of Formula I

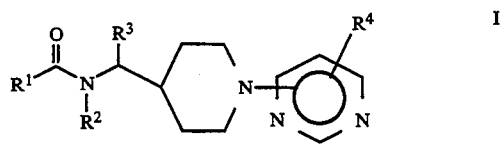

having psychocognitive properties, wherein $R^1$ is hydrogen, alkyl, bicycloalkyl, phenylalkyl, phenyl and pyridinyl; $R^2$ and $R^3$ are independently hydrogen or alkyl; and $R^4$ can be hydrogen, halogen, or trifluoromethyl. Compounds of Formula I can be incorporated into pharmaceutical compositions for use in enhancing cerebral function. Specific applications intended include restoration of cerebral function in dementia due to degenerative processes, diseases, trauma and the like; amnesia reversal; and improvement in memory and learning processes.

DETAILED DESCRIPTION OF THE INVENTION

In its broadest aspect, the present invention is concerned with acyclic amide derivatives of pyrimidinyl-piperazines having psychocognitive properties and being characterized by structural Formula I and pharmaceutically acceptable salts and/or solvates thereof.

In Formula I, $R^1$ can be hydrogen, lower alkyl, $C_{5-7}$ cycloalkyl, $C_{7-8}$ bicycloalkyl-methyl, phenyl-lower-alkyl, phenyl-hydroxy-lower alkyl, phenyl, and pyridinyl. Lower alkyl means alkyl residues containing from 1 to 4 carbon atoms. $C_{5-8}$ cycloalkyl would comprise cyclopentyl, cyclohexyl and cycloheptyl moieties. $C_{7-8}$ bicycloalkyl-methyl intends

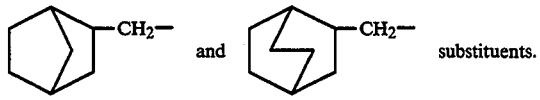

substituents.

By the phenyl-hydroxy-lower alkyl is meant phenylalkyl with a hydroxy functional group attached to the alkyl residue, e.g. a —CHPhCH$_2$OH moiety. $R^2$ and $R^3$ are independently selected and can be hydrogen or lower alkyl. $R^4$ can be hydrogen, halogen or trifluoromethyl. Halogen means F, Cl, Br, or I.

It is to be understood that the present invention is considered to include the various stereoisomers, e.g. optical isomers including individual enantiomers, mixtures of enantiomers, diastereomers, and mixture of diastereomers, which can arise as a consequence of structural asymmetry due to the presence of one or two asymmetric carbon atoms which may be incorporated in some compounds of the instant series. Separation of the individual isomers is accomplished by application of various methods which are well known to practitioners in the art. For medicinal use, the pharmaceutically acceptable acid addition salts, those salts in which the anion does not contribute significantly to toxicity or pharmacological activity of the organic cation may be preferred in some cases. The acid addition salts are obtained either by reaction of an organic base of structure I with an organic or inorganic acid, preferably by contact in solution, or by any of the standard methods detailed in the literature available to any practitioner skilled in the art. Examples of useful organic acids are carboxylic acids such as maleic acid, acetic acid, tartaric acid, propionic acid, fumaric acid, isethionic acid, succinic acid, pamoic acid, cyclamic acid, pivalic acid and the like; useful inorganic acids are hydrohalide acids such as HCl, HBr, HI; sulfuric acids; phosphoric acids; and the like. Additionally, the present invention also encompasses any of the Formula I compounds existing in solvate form such as a hydrate.

Synthesis

Various Formula I compounds can be prepared using the following synthetic routes or appropriate modifications thereof. In practice, the compounds of the present invention were made utilizing three somewhat different routes.

The first route (Scheme 1) proceeds via elaboration of a substituted amide onto an acylpyridine (XI). The resulting intermediate (VI) is catalytically reduced to a piperidine intermediate (II) and the pyrimidinyl group then appended by reaction with compound (III). This first route allows the rapid and convergent synthesis of compounds having varied substitution of the pyrimidinyl moiety.

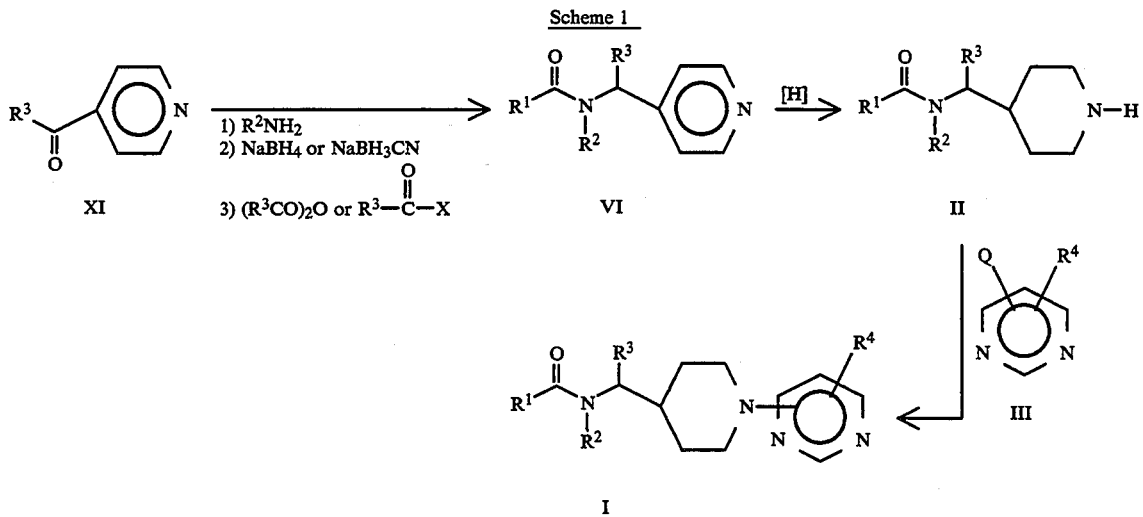

In this and subsequent schemes, $R^1$ through $R^4$ are as previously defined. Q is a suitable displacement group on the pyrimidine intermediate that is replaced by piperdine to couple the pyrimidinyl moiety to the piperidinyl nitrogen in elaboration of Formula I compounds.

A second route (Scheme 2) proceeds by the reductive amination of a 4-acylpyridine with protection of the resulting amine moiety, preferably by use of a t-butyloxycarbonyl (t-BOC) protecting group, to give compound X.

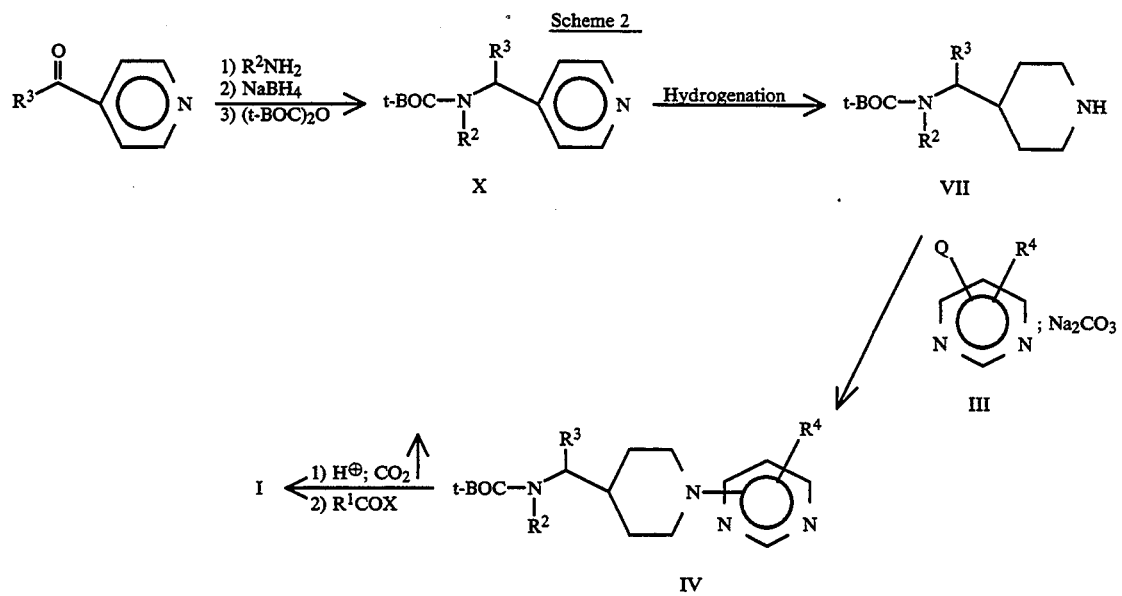

The pyridine ring of compound X is catalytically reduced to a piperidine ring, a preferable catalyst being $PTO_2$, to provide compound VII. The pyrimidinyl moiety is then appended, giving compound IV. Removal of the protective t-BOC group by treatment with aqueous acid, followed by acylation with $R^1COX$ wherein X is a synthetic organic leaving group. Preferred acylation reagents would be appropriate acyl halides. Acylation processes, reagents, and knowledge of leaving groups are all well known to one skilled in organic chemical synthesis. The advantage of the Scheme 2 synthesis is that a common intermediate such as IV can give rise to a variety of Compound I amides via the final step of the process.

Scheme 3 also can provide an array of Compound I products (wherein $R^2$ is H) from a common amine intermediate compound V.

$POCl_3$, and then reduced with a Rainey-nickel reduction to the primary amines of formula V. Standard acylation processes provided Formula I products.

Compounds of the instant invention have been evaluated for cerebral function enhancing activity using as a primary screen the reversal of electroconvulsive shock-induced amnesia for a stepdown passive avoidance response (cf: Banfis, et al. J. Pharmacol. Meth., 8, 255 (1982); Janvik, Ann. Rev. Psychol., 23, 457 (1972); and, McGaugh and Petrinovich, Int. Rev. Neurobiology, 8, 139 (1965)). Reference compounds such as pramiracetam, piracetam, aniracetam, etc., having activity in this paradigm have been purported to affect memory processes and may be useful in treating various dementias due to degenerative processes or diseases such as Alzheimer's disease.

In the test, rats were trained to remain immobile to

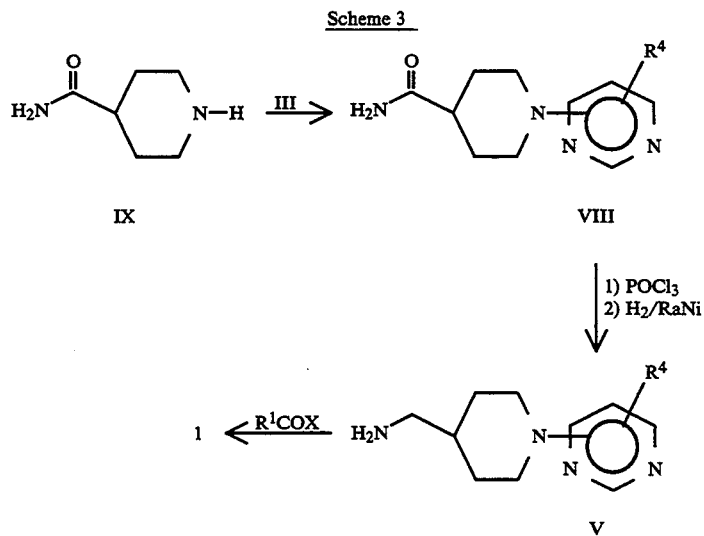

These amine compounds of Formula V were prepared by appending the pyrimidinyl moiety to isonipecotamide IX to give intermediates of Formula VIII which, while difficult to reduce, could be dehydrated to nitriles, using a dehydrating agent such as avoid electric foot shock. Two control groups were required: an ECS control and a sham-ECS (no ECS) control. ECS control animals were placed individually on a platform over an activated shock grid 30 minutes after vehicle or experimental drug administration. The animals readily stepped down from the platform, immediately experienced the foot shock, and quickly learned to escape to the platform. An animal was considered to have acquired the passive avoidance response if it remained on the platform for 2 minutes without stepping down following the foot shock delivery. Immediately after the acquisition, the ECS control animals were delivered ECS via oracular electrodes at an intensity of 75 mA for 800 msec. The sham-ECS control animals were treated in a manner identical to that described for the ECS controls, with the exception that current was not passed through the oracular electrodes. Both groups were administered a retention test 21 hours later. Animals were placed individually on the platform, and the latency to step down from the platform onto the unactivated shock grid was recorded; a given subject animal was considered to have retained the passive avoidance response if it remained on the platform for 120 seconds without stepping down. In general, vehicle treated rats not receiving ECS showed definite retention of response (83.5%), while vehicle treated animals receiving ECS displayed amnesia (17.5%) with regard to their ability to remember that descending the platform would result in a footshock. The active test compound were able to reverse the amnesiac effects of the ECS.

Results obtained from such testing, indicate that the compounds of formula I are useful in preventing amnesia which results from electroconvulsive shock. Such activity not only relates to memory retention in normal aging and senility processes but would be useful in protecting against the amnesia-producing effects of electroconvulsant shock as it is used clinically. Electroconvulsant shock is employed to treat some classes of psychiatric patients, particularly depressed patients who are refractory to traditional pharmacologic therapy. It is well documented that these electroconvulsant shock treatments induce the undesirable side-effect of amnesia in those patients to whom it is administered. The instant compounds which exhibit activity in protecting against the amnesia-producing effects of electroconvulsant shock in pharmacologic testing would be useful adjuncts to the clinical use of electroconvulsant shock in psychiatric treatment.

Further consideration of test results obtained for compounds of the present invention indicates their usefulness in several specific applications wherein such psychocognitive enhancement or normalizing effects on cerebral function would be highly desirable. The subject compounds are intended to be useful in treatment of dementias due to degenerative processes, diseases, and the like; with some specific examples being age-related memory dysfunction; AIDS-related dementia; multiple infarct dementia; Alzheimer's disease; Parkinson-related dementia; and the like. Similarly, the compounds are useful in enhancement of memory and learning processes and for acquisition of new information as well as treating deficits such as those encountered in benign senescent forgetfulness, learning disabilities and certain retardation states, e.g. minimal brain dysfunction. The compounds are also useful as antiamnesiacs and would find application against amnesias whether induced by ECS (a standard antidepressant treatment); drugs, e.g. benzodiazepines, alcohol, etc.; or trauma, e.g. head injury, post-neurosurgery, and so forth. Other uses which are envisioned for the compounds of this invention would be to treat miscellaneous disorders such as dyslexia, aphasia, and Tourette's syndrome.

In summary of the foregoing discussion, the instant compounds have cerebral function enhancing properties particularly suited to their use in treating dementias cognition and memory enhancement, reversal and/or prevention of amnesia and certain miscellaneous applications. Thus, another aspect of the instant invention concerns a process for enhancing cerebral function in a mammal in need of such treatment which comprises systemic administration to such mammal of an effective dose of a formula I compound or a pharmaceutically acceptable acid addition salt thereof. The administration and dosage regimen of compounds of formula I, is considered to be done in the same manner as for the reference compound piracetam, cf: Reisberg, et al, in Drug Development Research, 2475–480 (1982); Weng et al., in Rational Drug Therapy, 17(5), 1–4 (1983); Reisberg, et al., in "Psychopathology in the Aged", Editors, Cole and Barrett, Raven Press, New York, 243–245 (1980) and pramiracetam, cf: Butler, et al., J. Med. Chem., 27, 684–691 (1984).

The mode of systemic administration, dosage, and dosage regimen must in each case be carefully adjusted by utilization of sound professional judgment and consideration of the age, weight and condition of the recipient. Generally, the daily dose will be from about 0.1 g to about 10 g, preferably 0.5 g to 5 g, when given orally. In some instances, a sufficient therapeutic effect can be obtained at lower doses while in other, larger doses will be required. As is apparent to one skilled in clinical pharmacology, the amount of a formula I compound comprising the daily dose may be given in a single or divided dose taking into account those principles understood by the skilled practitioner and necessary for his practice of the art.

The term "systemic administration" as used herein refers to oral, sublingual, buccal, nasal, dermal, rectal, intramuscular, intravenous, and subcutaneous routes. Generally, it will be found that when a compound of the present invention is administered orally which is the preferred route, a slightly larger quantity of the active drug may be required to produce the same effect as a somewhat smaller quantity when given parenterally. In accordance with good clinical practice, it is preferred to administer the instant compounds at a concentration level which will produce effective beneficial effects without causing any harmful or untoward side effects.

Therapeutically, the instant compounds are generally given as pharmaceutical compositions comprised of an effective cerebral function enhancing amount of a compound of formula I or a pharmaceutically acceptable acid addition salt thereof and a pharmaceutically acceptable carrier. Pharmaceutical compositions for effecting such treatment will contain a major or minor amount (e.g. from 95% to 0.5%) of at least one compound of the present invention in combination with pharmaceutical carrier, the carrier comprising one or more solid, semi-solid, or liquid diluent, filler and formulation adjutant which is non-toxic, inert and pharmaceutically acceptable. Such pharmaceutical compositions are preferably in dosage unit forms; i.e. physically discrete units having a pre-determined amount of the drug corresponding to a fraction or multiple of the dose which is calculated to produce the desired therapeutic response. In usual practice, the dosage units contain 1, ½, ⅓, or less of a single dose. A single dose preferably contains an amount sufficient to produce the desired therapeutic effect upon administration at one application of one or more dosage units according to the predetermined dosage regimen, usually a whole, half, third, or less of the daily dosage administered once, twice, three or more times a day. It is envisioned that other therapeutic agents can also be present in such a composition. Pharmaceutical compositions which provide from 0.1 to 1 g of the active ingredient per unit dose are preferred and are conventionally prepared as tablets, lozenges, capsules, powders, aqueous or oily suspensions, syrups, elixirs, and aqueous solutions. Preferred oral compositions are in the form of tablets, capsules, and may contain conventional excipients such as binding agents, (e.g., syrup, acacia, gelatin, sorbitol, tragacanth, or polyvinylpyrrolidone), fillers (e.g. lactose, sugar, maize-starch, calcium phosphate, sorbitol or glycine), lubricants (e.g. magnesium stearate, talc, polyethylene glycol or silica), disintegrants (e.g. starch) and wetting agents (e.g. sodium lauryl sulfate). Solutions or suspensions of a formula I compound with conventional pharmaceutical vehicles are employed for parenteral compositions such as an aqueous solution for intravenous injection or an oily suspension for intramuscular injection. Such compositions having the desired clarity, stability and adaptability for parenteral use are obtained by dissolving from about 0.1% to 10% by weight of the active compound in water or a vehicle consisting of a polyhydric aliphatic alcohol such as glycerine, propylene glycol, and the polyethylene glycols or mixtures thereof. The polyethylene glycols consist of a mixture of non-volatile, usually liquid, polyethylene glycols which are soluble in both water and organic liquids and which have molecular weights from about 200 to 1500.

DESCRIPTION OF SPECIFIC EMBODIMENTS

The compounds which constitute this invention and their methods of preparation as well as their biological activity will appear more fully from a consideration of the following examples which are given for the purpose of illustration only and are not to be construed as limiting the invention in sphere or scope. All temperatures are understood to be in degrees C. when not specified. The nuclear magnetic resonance (NMR) spectral characteristics refer to chemical shifts ($\delta$) expressed in parts per million (ppm) versus tetramethylsilane (TMS) as reference standard. The relative area reported for the various shifts in the proton (PMR) spectral data corresponds to the number of hydrogen atoms of a particular functional type in the molecule. The nature of the shift as to multiplicity is reported as broad singlet (bs), singlet (s), multiplet (m), doublet (d), doublet of doublet (dd), triplet (t), or quartet (q). Abbreviations employed are DMSO-$d_6$ (perdeuterodimethyl-sulfoxide), CDCl$_3$ (deuterochloroform) and are otherwise conventional. The infrared (IR) spectral descriptions include only absorption wave numbers (cm$^{-1}$) having functional group identification value. The IR determinations were employed using potassium bromide (KBr) as diluent. All compounds gave satisfactory elemental analysis.

A. Scheme 1 Procedures:
1. Formula VI Compounds

EXAMPLE 1

N-Ethyl-N-[(4-pyridinyl)methyl]acetamide

A mixture of pyridine-4-carboxaldehyde (XI; 10.71 g, 0.1 mole) and ethyl amine (12.88 g of a 70% water solution, 0.2 mole) were stirred for 20 min. Cyclohexane (75 ml) was added and the mixture was refluxed for 16 hrs under a Dean-Stark trap. The mixture was then concentrated in vacuo. Ethanol (100 ml) and sodium borohydride (five 0.4 g tablets, 50 mmole) were then added to the residue and mixture was stirred for 3 hrs in an ice bath. The mixture was concentrated in vacuo and the residue was dissolved in acetonitrile (100 ml) and filtered. Acetic anhydride (10.38 ml, 0.11 mole) was added and the reaction was stirred for 2 days. Sodium carbonate (15.9 g, 0.15 mole) was added and the solution was refluxed for 20 min. The mixture was cooled and filtered. The filtrate was concentrated in vacuo and the residue was chromatographed on silica gel using 5% methanol/ethyl acetate as the eluent to give the product (14.57 g, 82%).

EXAMPLE 2

N-Methyl-N-[(4-pyridinyl)methyl]propionamide

Pyridine-4-carboxaldehyde, methyl amine, and propionic anhydride were reacted on a 0.1 mole scale in a manner similar to that given for Example 1 to give the desired amide (12.72 g, 72%).

EXAMPLE 3

N-Methyl-N-[1-(4-pyridinyl)ethyl]acetamide

Anhydrous ethyl amine (30 ml) was distilled into a 250 ml flask containing 4-acetylpyridine (6.06 g, 50 mmole). The mixture was diluted with methanol (30 ml) and then a solution of sodium cyanoborohydride (1.26 g in 15 ml of methanol) was added dropwise at 0°. The solution was allowed to warm to room temperature while stirring for 1 hr. TLC indicated much starting material remained, therefore another portion of sodium cyanoborohydride (1.26 g in 15 ml of methanol) was added. The solution was stirred for 2 hr more and then concentrated in vacuo. The residue was dissolved in methylene chloride (80 ml), filtered, and concentrated in vacuo. The residue was chromatographed on silica gel using 10% methanol/ethyl acetate as the eluent to give the 4-acetylpyridine starting material (2.31 g) and the desired amine (3.60 g, 53% overall yield, 85% based on unrecovered starting ketone). This amine intermediate (3.6 g, 26.5 mmole) was stirred for 18 hr in acetonitrile (20 ml) at room temperature with acetic anhydride (2.76 ml, 29.2 mmole). Excess Na$_2$CO$_3$ was added to the solution and the mixture was refluxed for 1 hr. The mixture was filtered and the filtrate was concentrated in vacuo to give the desired amide product as an oil (4.6 g, 97.5%) which was taken on without purification.

2. Formula II Compounds

EXAMPLE 4

N-Ethyl-N-[(4-piperidinyl)methylacetamide hydrochloride

A solution of the Example 1 amide (VI; 14.57 g, 82 mmole) in methanol (200 ml) and conc HCl (9.0 g, 170 mmole) was hydrogenated (60 psi) with platinum oxide (0.15 g) for 16 hrs. Another portion of platinum oxide (0.15 g) was then added and the mixture hydrogenated for 18 hrs more. The catalyst was filtered off and the filtrate was concentrated in vacuo to give the formula II product as a white powder (14.0 g, 80%).

EXAMPLE 5

N-Methyl-N-[(4-piperidinyl)methyl]propionamide hydrochloride

A solution of the amide of Example 2 (13.04 g, 73.3 mmole) in methanol (180 ml) and concentrated HCl (18.1 g) was reduced in a manner similar to that given for Example 4 to give the product II as a clear syrup (14.87 g, 92%) which was taken on without purification.

EXAMPLE 6

N-Methyl-N-[1-(4-piperidinyl)ethyl]acetamide

A solution of the amide of Example 3 (4.0 g 22.5 mmole) in methanol (50 ml) and concentrated HCl (6.0 g) was reduced in a manner similar to that given for Example 4 to give the solid formula II product (4.6 g, 92.3%).

3. Formula I Products

EXAMPLE 7

N-Ethyl-N-[[1-[2-(trifluoromethyl)-4-pyrimidinyl]-4-piperidinyl]methyl]-acetamide

A mixture of N-ethyl-N-[(4-piperidinyl)methyl]acetamide hydrochloride (Example 4; 2.14 g, 10 Mole), 4-chloro-2-trifluoromethylpyrimidine (1.83 g, 10 mmole), and sodium carbonate (2.65 g, 25 mmole) in DMF (30 ml) was stirred for 18 hrs at room temperature. The mixture was concentrated in vacuo. The residue was dissolved in methylene chloride (50 ml), filtered, and the filtrate was concentrated in vacuo. The residue was chromatographed on silica gel using ethyl acetate as the eluent to give formula I product as a yellow oil (2.17 g, 67%).

EXAMPLE 8

N-Ethyl-N-[[1-[2-(pyrimidinyl)-4-piperidinyl]methyl]-acetamide

A mixture of N-ethyl-N-[(4-piperidinyl)methyl]acetamide hydrochloride (Example 4; 5.36 g, 25 mmole), 2-chloropyrimidine (2.86 g, 25 mmole), and sodium carbonate (6.63 g, 62.5 mmole) were reacted in a manner similar to that given for Example 7. The crude product was chromatographed on silica gel using 1:3 hexane/ethyl acetate as the eluent to give product I as a viscous, yellow oil (4.65 g, 71%).

EXAMPLE 9

N-Methyl-N-[[1-(2-pyrimidinyl)-4-piperidinyl]methyl]-propionamide

A mixture of N-methyl-N-[(4-piperidinyl)methyl]-propionamide hydrochloride (Example 5; 3.68 g, 20 mmole), 2-chloropyrimidine (2.29 g, 20 mmole), and sodium carbonate (2.34 g, 22 mmole) were reacted in a manner similar to that given for Example 7. The crude product was chromatographed on silica gel using ethyl acetate as the eluent to give product I as a viscous, yellow oil (4.24 g, 81%).

EXAMPLE 10

N-Methyl-N-[[1-[2-(trifluoromethyl)-4-pyrimidinyl]-4-piperidinyl]methyl]-propionamide

A mixture of N-methyl-N-[(4-piperidinyl)methyl]-propionamide hydrochloride (Example 5; 1.66 g, 9 mmole), 4-chloro-4-(trifluoromethyl) pyrimidine (1.65 g, 9 mmole), and sodium carbonate (1.43 g, 13.5 mmole) were reacted in a manner similar to that given for Example 7. The crude product was chromatographed on silica gel using ethyl acetate as the eluent to give product as a clear viscous oil (1.85 g, 64%).

EXAMPLE 11

N-Methyl-N-[1-[1-(2-pyrimidinyl)-4-piperidinyl]ethyl]acetamide

A mixture of N-methyl-N-[1-(4-piperidinyl)ethyl]acetamide (Example 6; 2.3 g, 10.4 mmole), 2-chloropyrimidine (1.37 g, 12 mmole), and sodium carbonate (3.18 g, 30 mmole) were reacted in a manner similar to that given for Example 7. The crude product was chromatographed on silica gel using 5% methanol/ethyl acetate as the eluent to give product as a viscous, orange oil (1.57 g, 56.9%).

EXAMPLE 12

N-Methyl-N-[1-[1-[2-(trifluoromethyl)-4-pyrimidinyl]-4-piperidinyl]ethyl]-acetamide

A mixture of N-methyl-N-[1-(4-piperidinyl)ethyl]acetamide (Example 6; 2.3 g, 10.4 mmole), 4-chloro-2-(trifluoromethyl)-pyrimidine (2.19 g, 12 mmole), and sodium carbonate (3.18 g, 30 mmole) were reacted in a manner similar to that given for Example 7. The crude product was chromatographed on silica gel using 5% methanol/ethyl acetate as the eluent to give product as a viscous, orange oil (2.23 g, 63.9%).

B. Scheme 2 Procedures:

1. Formula X Compounds

EXAMPLE 13

N-(tert-Butyloxycarbonyl-N-ethyl-4-aminomethylpyridine

A mixture of pyridine-4-carboxaldehyde (26.78 g, 0.25 mole) and ethyl amine (32.2 g of a 70% water solution, 0.5 mole) were stirred for 20 min. Cyclohexane (250 ml) was added and the mixture was refluxed for 3 hrs under a Dean-Stark trap. The mixture was then concentrated in vacuo. Ethanol (250 ml) and sodium borohydride (thirteen 0.4 g tablets, 0.13 mole) were then added to the residue and mixture was stirred for 18 hrs. The mixture was concentrated in vacuo and the residue was dissolved in methylene chloride (250 ml) and filtered. The filtrate was concentrated in vacuo to give the product, N-ethyl-4-aminomethylpyridine (26.92 g, 79% which was taken on without purification.

Sodium bicarbonate (8.4 g, 0.1 mole) was added to a solution of crude N-ethyl-4-aminomethylpyridine (13.6 g, 0.1 mole) in methylene carbonate (200 ml). Di-tert-butyl dicarbonate (24.0 g, 1.1 mole) was then added and the mixture was stirred for 18 hrs. The mixture was filtered and the filtrate was concentrated in vacuo to give the crude product of formula X (23.0 g, 97%), which was taken on without purification.

2. Formula VII Compounds

EXAMPLE 14

N-(tert-Butyloxycarbonyl)-N-ethyl-4-aminomethylpiperidine

A solution of N-(t-BOC)-N-ethyl-4-aminoethylpyridine (Example 13; 20.5 g, 87 mmole) in methanol (150 ml) and aqueous HCl (87 ml of 1 N, 87 mmole) was hydrogenated (60 psi) for 18 hrs with platinum oxide (0.30 g). The mixture was filtered and the filtrate was stirred for 18 hrs with sodium carbonate (20 g). The mixture was filtered and the filtrate concentrated in vacuo to give piperidine product (19.16 g, 91%), which was taken on without purification.

Formula IV Compounds

EXAMPLE 15

N-Ethyl-N-[[1-(2-pyrimidinyl)-4-piperidinyl]methyl]amino-tert-butyl-carbamate

A mixture of N-(t-BOC)-N-ethyl-4-aminomethylpiperidine (Example 14; 23.0 g, 95 mmole), 2-chloropyrimidine (11.45 g, 100 mmole), and sodium carbonate (11.66 g, 110 mmole) in acetonitrile (200 ml) was stirred for 20 hrs and then refluxed for i hr. The mixture was cooled and filtered. The filtrate was concentrated in vacuo and the crude product was chromatographed on silica gel using ethyl acetate as the eluent to give IV product as green crystals (15.64 g, 51%).

EXAMPLE 16

N-Ethyl-N-[[1-[2-(trifluoromethyl)-4-pyrimidinyl]-4-piperidinyl]methyl]amine

A mixture of N-(t-BOC)-N-ethyl-4-aminomethylpiperidine (Example 14; 12.10, 50 mmole), 2-(trifluoromethyl)-4-chloropyrimidine (9.13 g, 50 mmole), and sodium carbonate (10.6 g, 100 mmole) in acetonitrile (100 ml) was stirred for 18 hrs and then refluxed for 2 hr. The mixture was cooled and filtered. The filtrate was concentrated in vacuo and the crude product was chromatographed on silica gel using ethyl acetate as the eluent to give IV product.

4. Formula I Products

EXAMPLE 17

N-Ethyl-N-[[1-(m-pyrimidinyl)-4-piperidinyl]methyl]-3-pyridinecarboxamide dihydrochloride hydrate A. N-Ethyl-[[1-(2-pyrimidinyl)-4-piperidinyl]methyl]amine A solution of N-ethyl-N-[[1-(2-pyrimidinyl)-4-piperidinyl]methyl]amino-t-butyl-carbamate, IV (Example 15; 15.64 g, 49 mmole) in methanol (50 ml) was added dropwise with stirring to concentrated HCl (170 ml) and the evolution of $CO_2$ was monitored through a gas bubbler. Approximately 10 min after the addition of IV was completed, the gas evolution has ceased. After 30 min, the solution was concentrated in vacuo, and the residue was dissolved in methanol (100 ml). This solution was stirred with sodium carbonate (15.0 g) for 30 min. The mixture was filtered and the filtrate was concentrated in vacuo. The residue was dissolved in methylene chloride (100 ml) and filtered to remove the inorganic salts. The filtrate was concentrated in vacuo to an oil which was Kügelrohr distilled to give the amine product as a pale yellow oil (9.50 g, 88%).

B. Thionyl chloride (13 ml, 180 mmole) was added to nicotinic acid (1.85 g, 15 mmole) and the mixture was heated in an 85° oil bath for 3 hrs. The solution was cooled and concentrated in 7acuo. The solid was dissolved in DMF (20 ml) and added to a mixture of N-Ethyl-[[1-(2-pyrimidinyl)-4-piperidinyl]methyl]amine (2.20 g, 10 mmole) and sodium carbonate (3.18 g, 30 mmole) in DMF (20 ml). After the mixture had stirred for 18 hrs, more sodium carbonate (3.2 g) was added and the mixture was heated to 80° for 1 hr. The mixture was cooled and filtered. The filtrate was concentrated in vacuo and the residue was chromatographed on silica gel using ethyl acetate as the eluent to give formula I product as a clear oil (2.03 g, 63%). The free base was converted to the diHCl salt using excess ethanolic HCl (mp: 100°–123°).

EXAMPLE 18

N-Ethyl-N-[[1-[2-(trifluoromethyl)-4-pyrimidinyl]-4-piperidinyl]methyl]-3-pyridinecarboxamide hydrochloride A. N-Ethyl-N-[[1-[2-(trifluoromethyl)-4-pyrimidinyl]-4-piperidinyl]methyl]amine(prepared in Example 16) was dissolved in methanol (50 ml) and concentrated HCl (20 ml) was added slowly. The mixture bubbled vigorously for 10 min, and was stirred for 1 hr. The solvent was then removed in vacuo. The residue was dissolved in methanol (100 ml) and refluxed with sodium carbonate (12.5 g) for 30 min. The mixture was cooled, filtered, and concentrated in vacuo. The residue was Kügelrohr distilled to give the amine product (9.85 g, 68%).

B. Nicotinic acid (6.16 g, 50 mmole) was refluxed in thionyl chloride (40 ml) for 3 hr. The excess thionyl chloride was removed in vacuo to give a white powder. DMF (90 ml) was added, followed by N-Ethyl-N-[[1-[2-(trifluoromethyl)-4-pyrimidinyl]-4-piperidinyl]methyl]amine (9.75 g, 33.8 mmole) and sodium carbonate (10.6 g, 100 mmole). The mixture was stirred for 18 hr and then was filtered and concentrated in vacuo. The residue was chromatographed on silica gel using 5% methanol/ethyl acetate to give formula I product (8.9 g, 67%). The free base was converted to the hydrochloride salt using excess ethanolic HCl to give a light brown powder (mp: 79°–110°).

EXAMPLE 19

N-Ethyl-2-(hydroxymethyl)-N-[[1-(2-pyrimidinyl)-4-pipermidinyl]methyl]benzeneacetamide hydrate Tropic acid (4.15 g, 25 mmole) was acetylated by stirring with acetyl chloride (2.13 ml, 30 mmole) and triethylamine (4.18 ml, 30 mmole) in acetonitrile (50 ml) for 4 hr. The solvent was removed in vacuo, the residue was dissolved in methylene chloride, and the solution was then filtered. The filtrate was concentrated in vacuo to give the acetyl ester of tropic acid (5.0 g, 96%). A mixture of this material (0.75 g, 3.6 mmole), N-ethyl-[[1-(2-pyrimidinyl)-4-piperidinyl]methyl]amine (See Example 17; 0.80 g, 3.6 mmole), 2-chloropyridinium methiodide (1.10 g, 4.3 mmole), and triethylamine (1.20 ml, 8.6 mmole), in methylene chloride (35 ml) was refluxed for 18 hr. The solvent was removed in vacuo and the residue was chromatographed on silica gel using 5% methanol/ethyl acetate as the eluent to give the desired amido-ester (0.6 g). This material was dissolved in methanol (40 ml) and concentrated $NH_4OH$ (10 ml). After stirring 18 hr, the solution was concentrated in vacuo and the residue was chromatographed on silica gel using 10% methanol/ethyl acetate as the eluent to give formula I product as a clear oil (0.32 g, 25%).

EXAMPLE 20

N-Ethyl-N-[[1-(2-pyrimidinyl)-4-piperidinyl]methyl]-formamide

Trigonelline (3-carboxy-1-methylpyridinium hydroxide inner salt; 3.47 g, 20 mmole) was refluxed in thionyl chloride (17 ml) for 4 hr. The excess thionyl chloride was removed in vacuo and then DMF (50 ml) was added followed by N-ethyl-[[1-(2-pyrimidinyl)-4- piperidinyl]methyl]amine (see Example 17; 3.30 g, 15 mmole) and sodium carbonate (4.75 g, 45 mmole). The mixture was heated to 70° for 20 hr and was then filtered and concentrated in vacuo. The residue was dissolved in 95% ethanol (500 ml) and stirred with sodium borohydride (2.12 g, 56 mmole) and 0° for 4 hrs. The solution was warmed to room temperature and more sodium borohydride (2.0 g) was added. The solution was refluxed 18 hrs, cooled, quenched with acetone, and filtered. The solution was concentrated in vacuo and the residue was chromatographed on silica gel using 5% methanol/ethyl acetate as the eluent to give an off white powder (0.90 g, 18%). This material proved not to be the expected trigonelline product, but was instead the formamide product of formula I.

C. Scheme 3 Procedures:
1. Formula VIII Compounds

EXAMPLE 21

1-[2-(Trifluoromethyl)-4-pyrimidinyl]-4piperidinecarboxamide

A mixture of isonepicotamide (IX; 7.94 g, 62 mmole), 4-chloro-2-(trifluoromethyl)pyrimidine (12.18 g, 66.7 mmole), and sodium carbonate (8.48 g, 80 mmole), in DMF (150 ml) was stirred at room temperature for 18 hr. The mixture was filtered and concentrated in vacuo. The residue was recrystallized from 2-propanol to give the amide VIII as white needles (14.75 g, 93%).

2. Formula V Compounds

EXAMPLE 22

1-[2-(Trifluoromethyl)-4-pyrimidinyl]-4-piperidinemethaneamine

The amide product of Example 21 (17.58 g, 64.2 mmole) was dissolved in DMF (180 ml) and POCl$_3$ (17.6 ml) was added. The exothermic solution turned deep red and was stirred for 18 hr. The solution was concentrated in vacuo and the residue was dissolved in methylene chloride. The solution was cooled in an ice bath as saturated sodium carbonate was added with stirring to quench the excess POCl$_3$. When the bubbling had stopped, the methylene chloride layer was separated and washed with water before being concentrated in vacuo. The residue was recrystallized from a mixture of ethyl acetate (25 ml) and cyclohexane (150 ml) to give the intermediate nitrile as pale yellow crystals (14.71 g, 90%). A solution of this intermediate (14.71 g, 57.5 mmole), in ethanol (200 ml) and concentrated ammonium hydroxide (10 ml), was hydrogenated (60 psi) over Raney nickel (10 g) for 18 hr. The catalyst was filtered off and the filtrate was concentrated in vacuo to give the amine product V (14.80 g, 99%) which was taken on with no further purification.

3. Formula I Products

EXAMPLE 23

2-[Bicyclo[2.2.1]heptan-2-yl]N-[[1-(2-pyrimidinyl)-4-piperidinyl]methyl]acetamide A solution of 2-norbornaneacetic acid (1.54 g, 10 mmole) and 1,1'-carbonyldiimidazole (1.62 g, 10 mmole) in methylene chloride (35 ml) was stirred for 15 min and then 1-(4-pyrimidinyl]-4-piperidinemethaneamine (V; 1.92 g, 10 mmole) was added. After stirring for 18 hrs the solution was diluted with methylene chloride (100 ml) and extracted with water (3×30 ml) and saturated sodium carbonate (30 ml). The methylene chloride layer was dried over magnesium sulfate and concentrated in vacuo to give a white solid. The crude product was recrystallized from a mixture of ethyl acetate (15 ml) and hexane (15 ml) to give the formula I product as a white powder (2.59 g, 79%, mp: 121°–126°).

By appropriate modification of the foregoing experimental procedures, additional compounds of the instant invention can be readily prepared.

We claim:

1. A compound of Formula I and the pharmaceutically

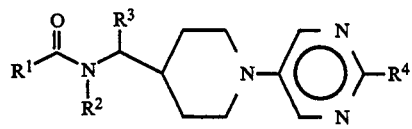

acceptable acid addition salts thereof wherein $R^1$ is selected from the group consisting of hydrogen $C_{1-4}$ alkyl, $C_{5-7}$ cycloalkyl, $C_{7-8}$ bicycloalkylmethyl, phenyl, phenyl-lower alkyl, phenylhydroxy-lower alkyl, and pyridinyl;

$R^2$ and $R^3$ are independently selected from hydrogen and $C_{1-4}$ alkyl; and $R^4$ is selected from hydrogen, halogen, or trifluoromethyl.

2. The compound of claim 1 wherein $R^1$ is $C_{1-4}$ alkyl.

3. The compound of claim 1 which is, N-ethyl-N-[[1-[2-(trifluoromethyl)-4-pyrimidinyl]-4-piperidinyl]methyl]-3-pyridinecarboxamide.

4. The compound of claim 1 which is 2-[Bicyclo[2.2.1]heptan-2-yl]-N-[[1-(2-pyrimidinyl)-4-piperidinyl]methyl]acetamide.

5. A compound of claim 2 selected from the group consisting of N-ethyl-N-[[1-[2-(trifluoromethyl)-4-pyrimidinyl]-4-piperidinyl]methyl]-acetamide; N-ethyl-N -[[1-[2-(pyrimidinyl)-4-piperidinyl]methyl]acetamide; N-methyl-N-[[1-(2-pyrimidinyl)-4-piperidinyl]methyl]-propionamide; N-methyl-N-[[1-[2-(trifluoromethyl)-4-pyrimidinyl]-4-piperidinyl] methyl]-propionamide; N-methyl-N-[1-[1-(2-pyrimidinyl)-4-piperidinyl]ethyl]acetamide; N-methyl -N-[1-[1-[2-(trifluoromethyl)-4-pyrimidinyl]-4-piperidinyl]ethyl]-acetamide.

6. The compound of claim 5, N-ethyl-N-[[1-[2-(pyrimidinyl)-4-piperidinyl]methyl]acetamide.

7. The compound of claim 5, N-methyl-N-[[1-[2-(trifluoromethyl)-4-pyrimidinyl]-4piperidinyl]methyl]-propionamide.

8. The compound of claim 5, N-methyl-N-[1-[1-[2-(trifluoromethyl)-4-pyrimidinyl]-4-piperidinyl]ethyl]acetamide.

9. A method for enhancing cerebral function in a mammal in need of such treatment which comprises systemic administration to the mammal of an effective dose of a compound claimed in claim 1.

10. A pharmaceutical composition for the enhancement of cerebral function comprising a pharmaceutical carrier and a compound according to claim 1.

* * * * *

UNITED STATES PATENT AND TRADEMARK OFFICE
CERTIFICATE OF CORRECTION

PATENT NO. : 5,338,738
DATED : August 16, 1994
INVENTOR(S): Ronald J. Matson et al It is certified that error appears in the above-identified patent and that said Letters Patent is hereby corrected as shown below:

On the cover page of the patent an inventor's name has been incorrectly spelled. The name Ronald J. Matson should be spelled as Ronald J. Mattson.

Signed and Sealed this

Eighteenth Day of October, 1994

Attest:

BRUCE LEHMAN

*Attesting Officer*   *Commissioner of Patents and Trademarks*